United States Patent [19]

Erath

[11] 4,099,117
[45] Jul. 4, 1978

[54] METHOD AND APPARATUS FOR MEASURING THE QUALITY OF INSULATION ON A BURIED PIPELINE AND THE QUANTITY OF METAL OXIDE PRESENT AT BREAKS IN THE INSULATION

[75] Inventor: Louis W. Erath, 5714 Green Ash, Houston, Tex. 77036

[73] Assignees: Dick Gaut, Marrero, La.; Louis W. Erath; Maurice C. Bierman, Jr., both of Houston, Tex.

[21] Appl. No.: 680,487

[22] Filed: Apr. 26, 1976

[51] Int. Cl.$^2$ .................... G01R 31/12; G01R 31/08
[52] U.S. Cl. ................................ 324/54; 324/9; 324/52
[58] Field of Search ............... 324/1, 9, 52, 54, 65 R, 324/65 CR, 71 R

[56] References Cited

U.S. PATENT DOCUMENTS

| | | | |
|---|---|---|---|
| 2,378,440 | 6/1945 | Scott | 324/9 X |
| 3,299,351 | 1/1967 | Williams | 324/52 |
| 3,526,831 | 9/1970 | Smith | 324/52 X |
| 3,792,350 | 2/1974 | Bossler et al. | 324/52 |
| 3,862,491 | 1/1975 | Richardson | 324/54 X |
| 3,866,117 | 2/1975 | Erdman | 324/54 |
| 3,991,363 | 11/1976 | Lathrop | 324/54 X |

*Primary Examiner*—Gerard R. Strecker
*Attorney, Agent, or Firm*—Jennings B. Thompson

[57] ABSTRACT

The invention disclosed comprises a method of and apparatus for inspecting a pipeline in situ. An alternating voltage is impressed between the pipeline and a ground bed. Spaced electrodes are positioned transverse the pipeline at spaced locations along the pipeline. At each location, the current flowing between the electrodes is used to indicate the condition of the coating on the pipeline. In one aspect of the invention, the current flowing between electrodes is obtained by measuring the resistance of the medium in which the pipeline is buried, such as the ground, and the voltage, and then dividing the voltage by the resistance. In another aspect of the invention, the ratio of the resistive and reactive components of the current flowing between the pipeline and the ground bed is used to indicate the quality of the pipeline coating. In yet another aspect of the invention, the third harmonic content of the voltage is measured to obtain an indication of the presence of iron oxide. The amount of third harmonic present when compared with current flow indicates the quantity of oxide.

10 Claims, 5 Drawing Figures

METHOD AND APPARATUS FOR MEASURING THE QUALITY OF INSULATION ON A BURIED PIPELINE AND THE QUANTITY OF METAL OXIDE PRESENT AT BREAKS IN THE INSULATION

This invention relates generally to the inspection of buried pipelines in place. In one of its aspects, this invention relates to the location of breaks or openings in the external coating of a pipeline. In another aspect, this invention relates to a method of and apparatus for indicating the presence of metal oxide formed on the pipeline at such breaks in the coating. In yet another aspect of this invention, it relates to a determination of the quality of the coating on the pipeline.

Pipelines are used extensively to transport liquids and gases from one place to the other. With very few exceptions, all pipelines are buried in the ground. Even those that are used to transport hydrocarbons produced offshore are buried beneath the ocean floor for much of their length. Most pipelines are made of a material, such as steel, that will suffer external corrosion when buried in the ground. Some soils, of course, are much more corrosive than others depending upon the moisture content thereof and other factors. Corrosion reduces the physical strength of the pipeline and, if allowed to proceed, will eventually cause the pipe to fail. Therefore, it is standard practice to provide protection to pipelines, particularly those that carry dangerous, flammable materials under pressure, such as crude oil, crude oil products, and natural gas.

These pipelines are protected in two ways. First, they are provided with a protective coating before they are buried in the ground. Second, cathodic protection devices are used to supplement the protection offered by the external coatings by reducing electrolytic corrosion. As time goes by, however, since the pipeline is buried and out of sight, no one knows how good a job the protective coating and cathodic protection system is doing in preventing corrosion of the pipeline. Therefore, periodically, pipelines, particularly those that carry potentially explosive products under high pressure, are subjected to hydrostatic pressure testing. In this process, a section of the line is isolated, the line is filled with water, and the line is then subjected to a preselected hydrostatic pressure. If the line does not fail, then it is placed back in service. This is obviously a very expensive and time consuming method of testing or inspecting a pipeline. Further, it takes the pipeline out of service during the time the test is being conducted. Another disadvantage is the obvious waste of water. Further, should the line fail under the test, it is often very difficult to locate the break since the section being tested may be thousands of feet long and located where a break would not be readily apparent at the surface, as for example, where the line is located in a marshy or underwater area.

It is an object of this invention to provide a method of and apparatus for inspecting buried pipelines in situ from the surface of the ground or the surface of the sea bed should the line be buried underneath a body of water.

It is a further object of this invention to provide a method of and apparatus for inspecting a buried pipeline that does not require that the pipeline be taken out of service and that will indicate the location of openings or breaks in the coating of the pipeline accurately so that the pipeline can be quickly and easily uncovered to repair the break in the coating with a minimum of excavation.

It is another object of this invention to provide a method of and apparatus for obtaining an indication on the amount of oxide that has formed on the pipeline where there has been a break in the coating so it can be determined if the corrosion has progressed sufficiently to require corrective measures.

It is another object and advantage of this invention to provide a method of and apparatus for indicating the quality of the coating on the pipeline to see if the coating is still in good shape or has generally deteriorated even though there is no actual break in the coating.

These and other objects, advantages, and features of this invention will be apparent to those skilled in the art from a consideration of this specification, including the attached drawings and appended claims.

Figure 1:
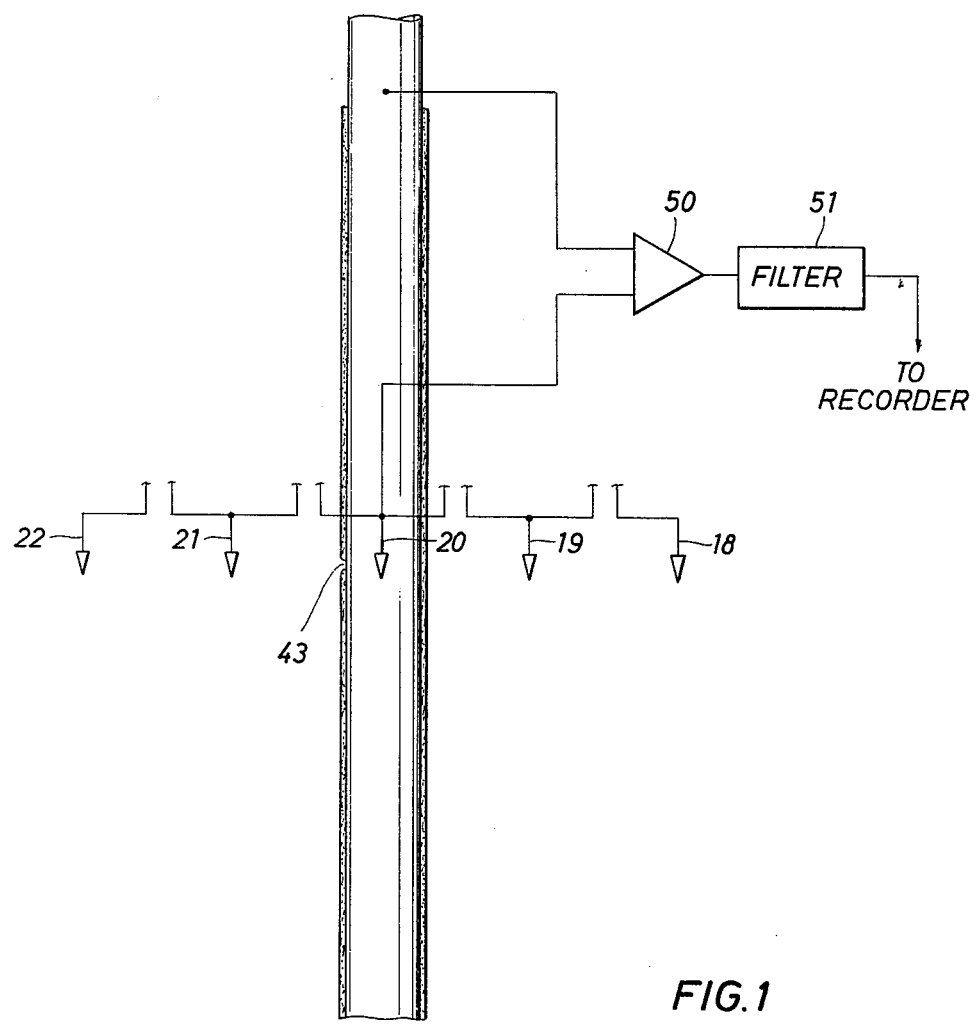
FIG. 1 is a schematic drawing of how the apparatus of the invention is positioned relative to the pipeline to be inspected.

The general arrangement of the apparatus for the practice of this invention is shown in FIG. 1. Generator 10 is connected between pipeline 12 and ground bed 14 to impress an alternating current voltage between pipeline 12 and the ground bed. It is understood that the pipeline is buried, usually in the ground. As used herein, "ground" is intended to include any medium in which a pipeline may be buried, even water. To practice the invention, the medium must be at least a better conductor than the coating on the pipeline. If the pipeline is equipped with a cathodic protection system, there will be connections between the pipeline and ground bed spaced along the pipeline. These are convenient locations for connecting generator 10 between the pipeline and a ground bed buried in the medium in which the pipeline is buried.

Filter 16 is tuned to filter out a particular harmonic from the impressed voltage. In the case of steel pipe, it is the third harmonic. Preferably, the generator circuit should be arranged to impress as pure a sinusoidal voltage between the pipeline and the ground as can be practically obtained. Most pipelines are made of metal alloys, which are good conductors. The external coating, however, is purposely selected from materials that are poor conductors and therefore the coating acts as a dielectric between the pipeline and the ground.

The apparatus includes a plurality of electrodes. In the embodiment shown in FIG. 1, five such electrodes 18, 19, 20, 21, and 22 are used. These electrodes are mounted so that they can be inserted into the ground above the pipeline along a line transverse the longitudinal axis of the line. The electrodes are equally spaced. Generally, an odd number of electrodes will be used so that the middle electrode can be positioned approximately directly above the pipeline. The electrodes are electrically connected to various electronic circuits, shown in FIGS. 2A, 2B, and 3, which will be described below. They are designed to make good electrical contact with the ground. The electrodes are mounted for movement along the longitudinal axis of the pipeline so that they can be placed in contact with the ground at spaced intervals along the pipeline. The distance between each location of the electrodes for this purpose will vary with conditions, such as the type of soil, the depth of the pipeline, etc.

Figure 2:
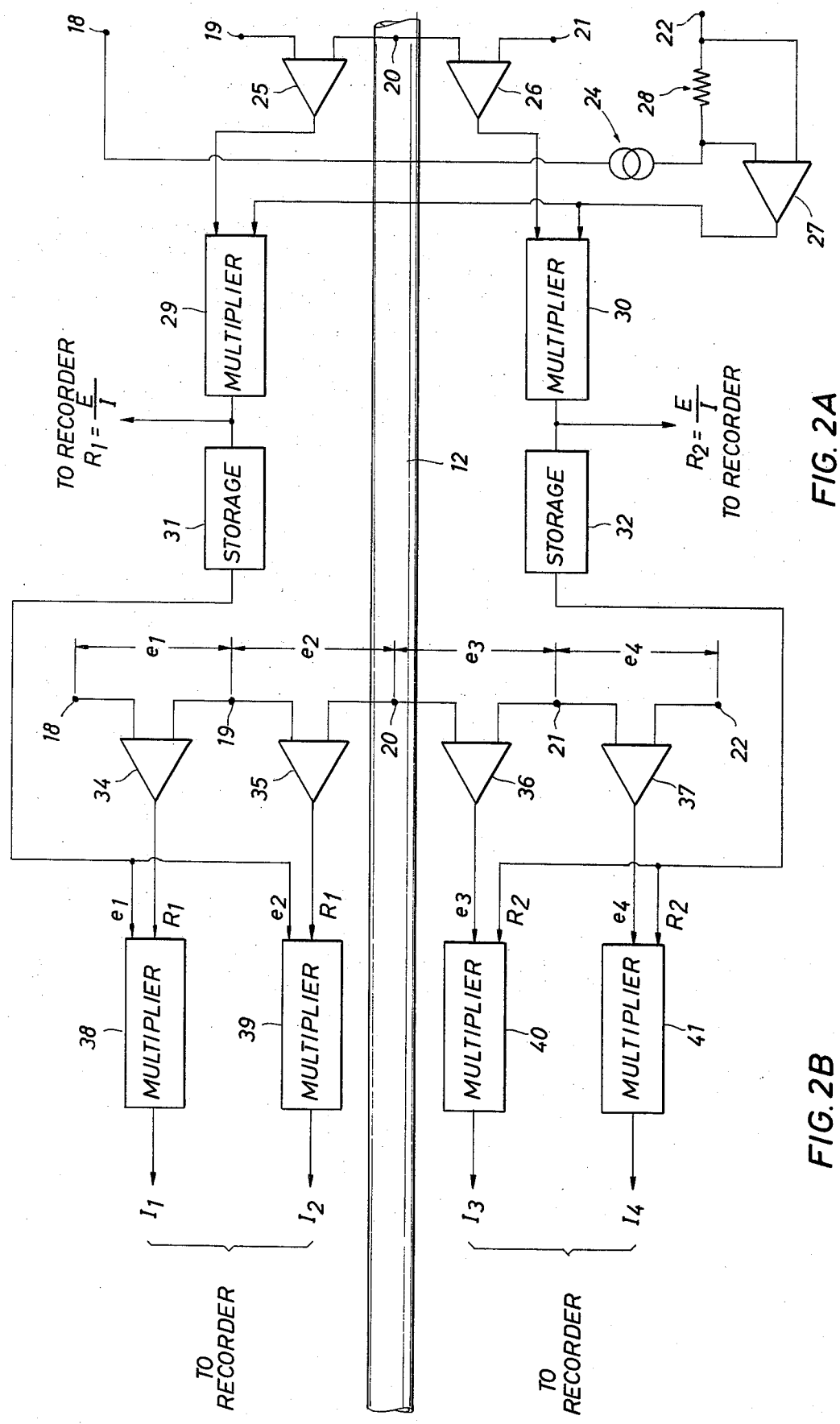
FIGS. 2A and 2B are diagrams of electrical circuits employed to practice one aspect of the invention.
Figure 3:
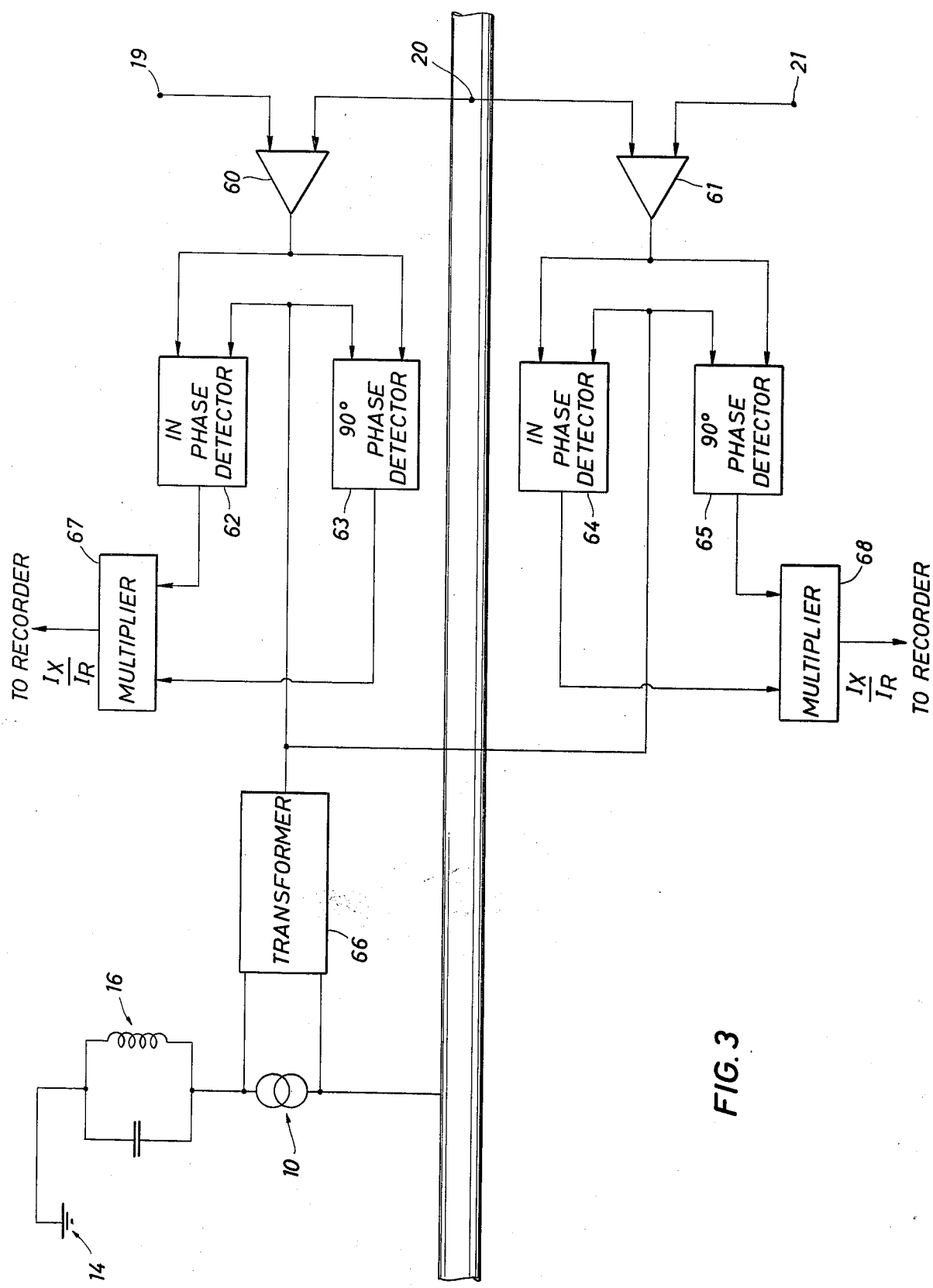
FIG. 3 is a circuit diagram of apparatus employed to practice another aspect of the invention.

As stated above, one aspect of this invention is to provide a method of and apparatus for indicating breaks or openings in the external coating of a buried pipeline. One embodiment of such apparatus is shown in FIGS. 1 and 2. In accordance with this embodiment of the invention, the method includes the step of determining the resistance of the ground in which the electrodes are located. The apparatus for accomplishing this is shown in FIG. 2A.

Figure 4:
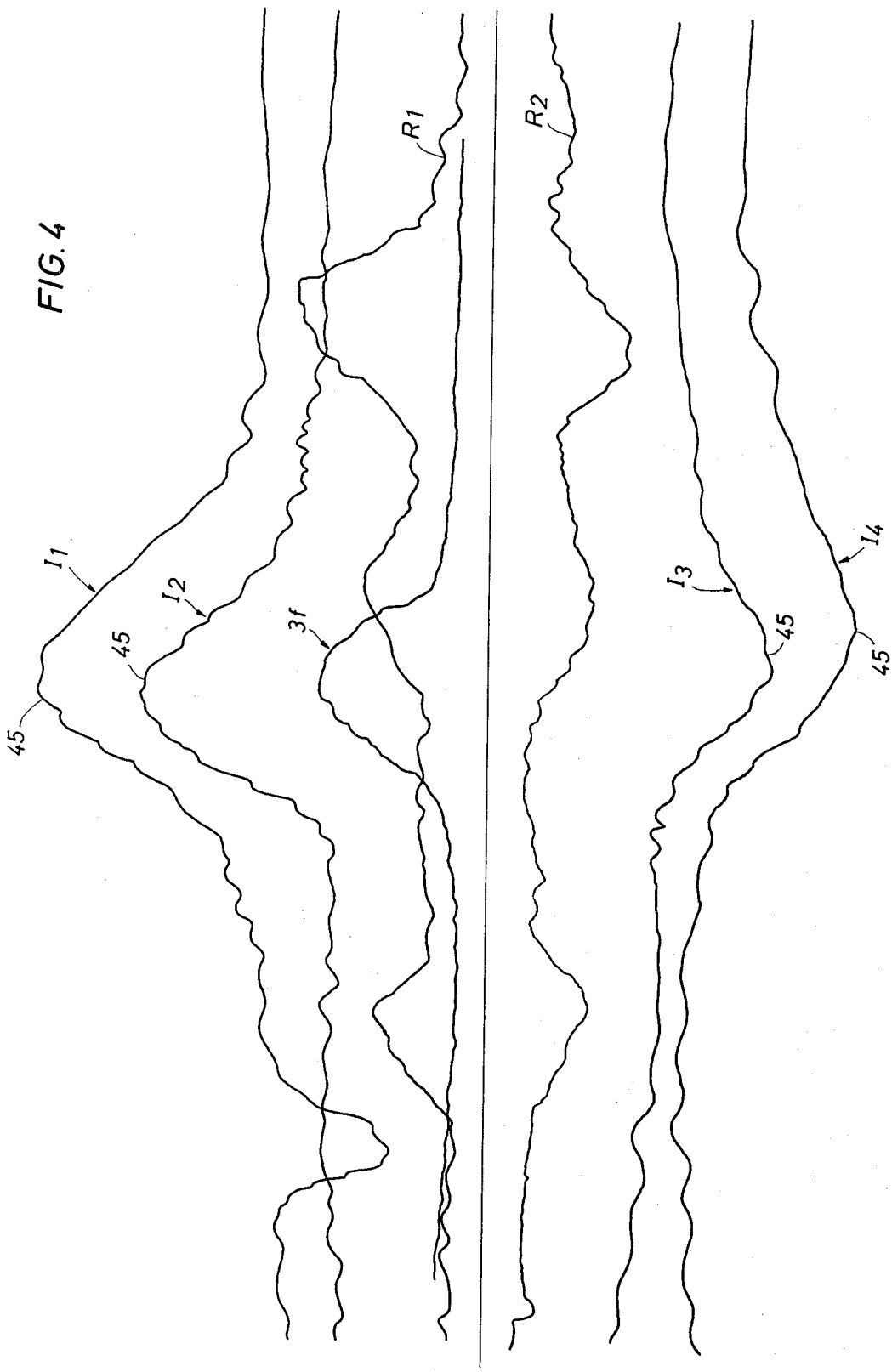
FIG. 4 illustrates the preferred manner of recording the information obtained by the method and apparatus of this invention to indicate breaks in the coating, the presence of metal oxides, and the quality of the coating.

Generator 24 impresses an alternating current voltage, preferably of relatively low frequency, between electrodes 18 and 22, the two outside electrodes. This causes a current to flow between the electrodes. Amplifiers 25 and 26 sense the voltage drop between electrodes 19 and 20 and electrodes 20 and 21, respectively. Amplifier 27, along with resistor 28, senses the current flow between the two outside electrodes. This information is fed to multipliers 29 and 30. There the voltage between electrodes 19 and 20 is divided to provide an output signal $R_1$, that is proportional to the resistance of the ground between the electrodes. In the same manner, the voltage between electrodes 20 and 21 is divided by the current to provide signal $R_2$ that is proportional to the resistance of the ground between electrodes 20 and 21. This signal is transmitted to the recorder where it is printed on a strip chart, as shown in FIG. 4, and to digital storage units 31 and 32 for later use.

After the resistance of the ground between the electrodes has been obtained, the electrodes are switched into the circuit shown in FIG. 2B where four amplifiers 34, 35, 36, and 37 are connected to the electrodes in the manner shown.

These amplifiers sense the potential between adjacent electrodes $e_1 - e_4$ created by the voltage impressed between the pipeline and the ground by generator 10, as shown in FIG. 1. The potential sensed by the amplifiers is supplied to multipliers 38, 39, 40, and 41. There, the potential drop between each two adjacent electrodes is divided by the appropriate resistance $R_1$ or $R_2$ to obtain signals $I_1$, $I_2$, $I_3$, and $I_4$ that are proportional to the current flowing between the electrodes from the impressed voltage from generator 10. Note that potentials $e_1$ and $e_2$ were divided by $R_1$ since this resistance was obtained from between electrodes 19 and 20 on the same side of the pipeline. For the same reason, $R_2$ is used with $e_3$ and $e_4$. All of these current signals are transmitted to a recorder where they are graphically illustrated, as shown in FIG. 4, on a strip chart along with the earth's resistance $R_1$ and $R_2$. The portion of the strip chart shown in FIG. 4 shows the change in the value of the currents that would be produced by a hole in the external protective coating of the pipeline. For example, assume that there was a hole, such as indicated at 43 in FIG. 1. Since the protective coating has a high dielectric strength, if the coating is sound the flow of current through the ground between the ground bed and the pipe will be relatively low. If there is an opening in the coating, however, such as the one indicated at 43, the flow of current in the ground will increase due to the absence of coating material. This increase in current flow is indicated by peaks 45 in the measured current.

As shown, each current $I_1 - I_4$ increases. Thus, this is a very good indication that there has been a break in the coating. It is possible, of course, that one or two of the current flows could change, and this would not necessarily mean a break in the coating but could be caused by other factors. By printing out all four values of current, for easy comparison, the fluxuation of the currents can be quickly and easily interpreted and compared to changes in ground resistance to reduce the possibility of spurious indications of faults in the coating.

As explained above, the increase in current flows that produced peaks 45, indicates that there is an opening or break in the coating on the pipeline. It may be, however, that the soil in which this particular portion of the pipeline is buried is not very corrosive and, consequently, little or no corrosion may have occurred. If so, it would not be worthwhile to dig up the pipeline to repair this break. Therefore, it is another aspect and feature of this invention to provide a method of and apparatus for determining the presence and quantity of metal oxide formed on the pipeline. Generally, corrosion is the oxidation of the major metallic component of the material. The corrosion of steel pipelines converts the iron in the steel to ferric oxide or rust. It has been determined that metal oxides will produce harmonics in an alternating current flowing through them. Ferric or iron oxide produces the third harmonic. Therefore, apparatus is provided to monitor the harmonic content of the voltage impressed on the pipeline as the electrodes move down the pipeline. As shown in FIG. 1, amplifier 50 is connected between pipeline 12 and electrode 20. Other electrodes could be used. The idea is simply to monitor the signal traveling between the pipeline and the ground. This signal is passed through filter 51 which is tuned to pass the particular harmonic desired, such as the third harmonic signal in the case of steel pipe. This signal, 3f, is then printed out on the strip chart, as shown in FIG. 4.

As stated above, the presence of the third harmonic is an indication of the presence of iron oxide, but the strength of the harmonic signal must be compared with the strength of the current flow in order to determine the quantity of oxide present. Therefore, this information is printed out on the strip chart in the manner shown and by comparing the strength of the third harmonic signal with that of the current signal, a determination can be made as to whether or not oxidation has progressed to the point that the line should be repaired. For pipelines that are made of an alloy that is high in a metal other than iron, the harmonic can be monitored that is produced by the oxide of that metal. For example, copper oxide produces the second harmonic.

Thus, in accordance with the above-described apparatus, the method of inspecting a buried pipeline includes the steps of impressing an alternating current between the pipeline and a ground bed, measuring the earth's resistance between selected spots in the ground above the pipeline, and measuring the voltage drop between such selected points to obtain an indication of current flow through the ground adjacent the pipeline which can be used as an indication of whether or not the external coating on the pipeline is intact or whether or not there happens to be a break in such coating. In addition, the harmonic content of the signal is monitored to obtain an indication of oxide build-up on the pipeline.

In accordance with another aspect of this invention, the overall quality of the coating can be determined. In the embodiment shown in FIG. 3, electrodes 19 and 20 are connected through amplifier 60 to phase detectors 62 and 63. Electrodes 20 and 21 are connected through amplifier 61 to phase detectors 64 and 65. Transformer 66 provides the phase detectors with a reference signal of the impressed frequency. Phase detectors 62 and 64 provide the in-phase component, $I_R$, of the currents flowing between the electrodes. Phase detectors 63 and 65 provide the component $I_X$ of the currents flowing between the electrodes that is 90° out-of-phase. Multipliers 67 and 68 divide the component that is 90° out-of-phase, $I_X$ by the in-phase component $I_R$. The ratio thus obtained is an indication of the condition of the coating. The in-phase current is, of course, a function of the resistance. The out-of-phase current $I_X$ is a function of the reactance in the circuit. If the coating is in good condition, the resistive component will be small and the reactive component large. Conversely, if the coating has deteriorated, even though it hasn't been breached, the resistive component will increase while the reactive component decreases. Thus, by definition, the electrical quality of the pipeline coating is equal to the ratio of the reactive component of the current to the resistive component of the current, as produced by a voltage source of frequency $f$.

The current ratios may be plotted on a strip chart and an indication of the quality of the coating obtained. Breaks in the coating will be indicated by a substantial drop in the value of the ratios of the currents. Alternatively, the ratios can be printed along with all the information previously discussed above to obtain an additional check of the condition of the pipelines and another way of cross-checking the information to reduce the chance of spurious readings.

With a fixed ground bed, as the electrodes move away along the pipeline, the current flow will decrease inherently. For this reason, the ground bed and connection to the pipeline will have to be moved periodically. The ground could be carried along with the electrodes. The connection to the pipeline, however, will have to be made at the cathodic protection connections, valves, or the like.

From the foregoing, it will be seen that this invention is one well adapted to attain all of the ends and objects hereinabove set forth, together with other advantages which are obvious and which are inherent to the apparatus.

It will be understood that certain features and subcombinations are of utility and may be employed without reference to other features and subcombinations. This is contemplated by and is within the scope of the claims.

As many possible embodiments may be made of the invention without departing from the scope thereof, it is to be understood that all matter herein set forth or shown in the accompanying drawings is to be interpreted as illustrative and not in a limiting sense.

The invention now having been described, what is claimed is:

1. A method of inspecting in situ an externally coated metal pipeline that is buried in an electrically conductive medium, such as the ground, comprising connecting the pipeline to a source of alternating electrical voltage, connecting the voltage source to a ground bed located in the medium, and measuring along the pipeline the flow of electrical current through the medium between the ground bed and the pipeline to locate breaks in the coating of the pipeline by changes in the current flow, and measuring one of the harmonics in the signal that is produced by an oxide of the metal of the pipeline to obtain an indication of the amount of metal oxide formed at the break in the coating.

2. The method of claim 1 in which the third harmonic is measured to obtain an indication of the iron oxide formed at the break in the coating.

3. The method of determining the presence of a selected metal oxide formed on a buried pipeline comprising connecting the pipeline to a source of alternating voltage, filtering the harmonic from the alternating voltage that is produced by the selected metal oxide, connecting such source to a ground bed, and measuring the oxide produced harmonic content of the alternating voltage flowing through the ground between the pipeline and the ground bed at selected locations to obtain an indication of the presence of the selected metal oxide from the oxide produced harmonic content of the voltage.

4. A method of inspecting an externally coated pipeline made of an iron containing metal that is buried in an electrically conductive medium, such as the ground, comprising connecting the pipeline to a source of alternating electrical voltage, connecting the voltage source to a ground bed located in the medium, and measuring the flow of electrical current through the medium between the ground bed and the pipeline along the path of the pipeline to locate breaks in the coating of the pipeline by changes in the current flow, and measuring the third harmonic content of the voltage that is produced by an oxide of the metal of the pipeline to obtain an indication of the amount of iron oxide present at each break located in the coating.

5. A method of inspecting for breaks in the external protective coating of a buried metal pipeline comprising connecting the pipeline at a selected point to a source of alternating electrical voltage, connecting the electrical voltage source to a ground bed spaced from the pipeline, inserting a plurality of spaced electrodes into the ground above the pipeline at spaced locations along a line transverse the longitudinal axis of the pipeline, and at each location measuring the resistivity of the ground between the electrodes, measuring the voltage between adjacent electrodes, calculating the current flow between adjacent electrodes from the ground resistivity and the voltage and comparing the current measured at each location to determine if the current flow at any location is such as would indicate a break in the coating adjacent such location, and measuring at each location one of the harmonics in signal that is produced by an oxide of the metal of the pipeline and comparing the value of such signal with the amount of current flow to get an indication of the amount of metal oxide formed at any break indicated in the coating.

6. The method of claim 5 in which the third harmonic frequency is measured to determine the amount of iron oxide formed at any break indicated.

7. Apparatus for inspecting in situ an externally coated pipeline made of an iron containing metal that is located in an electrically conductive medium such as the ground or along the bottom of the ocean, comprising a sinusoidal alternating electrical voltage connected between the pipeline and a ground bed in the medium, a plurality of electrodes spaced along a line transverse the direction of the longitudinal axis of the pipeline for positioning in the medium at selected locations along the direction of the pipeline, means for measuring the current flowing between the electrodes at each location to obtain indications of changes in resistance that indicate a break in the coating on the pipeline, means for detecting the voltage signal between two of said electrodes, and means for measuring the third harmonic component of said signal that is produced by iron oxide to determine the presence of iron oxide and for comparing the component with the current flow to indicate the amount of iron oxide present.

8. The apparatus of claim 7 in which at least three electrodes are used with the center electrode located approximately over the pipeline and the means for measuring the amount of current flowing between each electrode includes means for placing a known voltage between the intermost electrodes, means for measuring the voltage between adjacent electrodes, and means for determining the resistance of the medium between adjacent electrodes based on the current flow and voltage.

9. A method of inspecting the external coating of a pipeline buried in an electrically conductive medium comprising the steps of impressing an alternating voltage between the pipeline and ground, measuring the voltage between selected points in the medium along a line transverse the longitudinal axis of the pipeline, resolving the measured voltage into its resistive component and its reactive component, and obtaining a signal proportional to the ratio of the resistive component to the reactive component which indicates the quality of the external coating of the pipeline and is independent of the resistivity of the medium.

10. The method of claim 9 further including measuring the harmonic content of the voltage that is produced by oxides of the metal of the pipeline to obtain an indication of the presence of and the quantity of oxide on the pipeline.

* * * * *